US006667805B2

(12) United States Patent
Norton et al.

(10) Patent No.: US 6,667,805 B2
(45) Date of Patent: Dec. 23, 2003

(54) SMALL-SPOT SPECTROMETRY INSTRUMENT WITH REDUCED POLARIZATION

(75) Inventors: Adam E. Norton, Palo Alto, CA (US); Kenneth C. Johnson, Santa Clara, CA (US); Fred E. Stanke, Cupertino, CA (US)

(73) Assignee: Sensys Instruments Corporation, Santa Clara, CA (US)

( * ) Notice: Subject to any disclaimer, the term of this patent is extended or adjusted under 35 U.S.C. 154(b) by 147 days.

(21) Appl. No.: 09/932,548

(22) Filed: Aug. 17, 2001

(65) Prior Publication Data

US 2002/0021441 A1 Feb. 21, 2002

Related U.S. Application Data

(60) Provisional application No. 60/226,396, filed on Aug. 18, 2000.

(51) Int. Cl.[7] .................................................. G01J 3/28
(52) U.S. Cl. ............................. 356/326; 359/368
(58) Field of Search ............................ 356/326; 359/368

(56) References Cited

U.S. PATENT DOCUMENTS

| 4,572,608 | A |   | 2/1986  | Mochizuki et al. ...... 350/96.15 |
| 4,712,912 | A |   | 12/1987 | Messerschmidt ............ 356/73  |
| 4,818,169 | A | * | 4/1989  | Schram et al. .............. 359/392 |
| 4,922,309 | A |   | 5/1990  | Sekiwa et al. .............. 356/300 |
| 5,037,200 | A |   | 8/1991  | Kodama ..................... 356/252 |
| 5,218,652 | A |   | 6/1993  | Lutz ............................ 385/11 |
| 5,243,465 | A | * | 9/1993  | Fein ............................. 359/350 |
| 5,430,795 | A |   | 7/1995  | Taga et al. ................... 359/179 |
| 5,638,207 | A |   | 6/1997  | Fukuzawa et al. ........... 359/375 |
| 5,657,121 | A |   | 8/1997  | Nishina ....................... 356/327 |
| 5,834,758 | A |   | 11/1998 | Trulson et al. ............. 250/201.2 |
| 5,933,555 | A |   | 8/1999  | Shen ............................ 385/32  |
| 6,040,906 | A |   | 3/2000  | Harhay ......................... 356/301 |
| 6,075,646 | A | * | 6/2000  | Suzuki ......................... 359/368 |

FOREIGN PATENT DOCUMENTS

| EP | 0 665 452 A1 | 1/1995  | ............ G02B/6/26  |
| JP | 1-287528     | 11/1989 | ............ G02B/27/28 |
| JP | 4-358115     | 12/1992 | ............ G02B/27/28 |
| JP | 5-257066     | * 10/1993 | ............ G02B/21/00 |

OTHER PUBLICATIONS

M.E. Lee et al., "Analysis of Reflectometry and Ellipsometry Data from Patterned Structures", Univ. of Michigan, Dept. of Elect. and Computer Science, pp. 1–5.
Product page of Varian Website, "Polarizer and Depolarizer Accessory", pp. 1–2.
Nasa Research Announcement, "Technical Details on OMI and Other EOS Chem Instruments", Sep. 29, 1999, pp. 1–2.

* cited by examiner

Primary Examiner—F. L. Evans
Assistant Examiner—Kara Geisel
(74) Attorney, Agent, or Firm—Stallman & Pollock LLP

(57) ABSTRACT

A small-spot imaging, spectrometry instrument for measuring properties of a sample has a polarization-scrambling element, such as a Lyot depolarizer, incorporated between the polarization-introducing components of the system, such as the beamsplitter, and the microscope objective of the system. The Lyot depolarizer varies polarization with wavelength. Sinusoidal perturbation in the resulting measured spectrum can be removed by data processing techniques or, if the depolarizer is thick or highly birefringent, may be narrower than the wavelength resolution of the instrument.

25 Claims, 2 Drawing Sheets

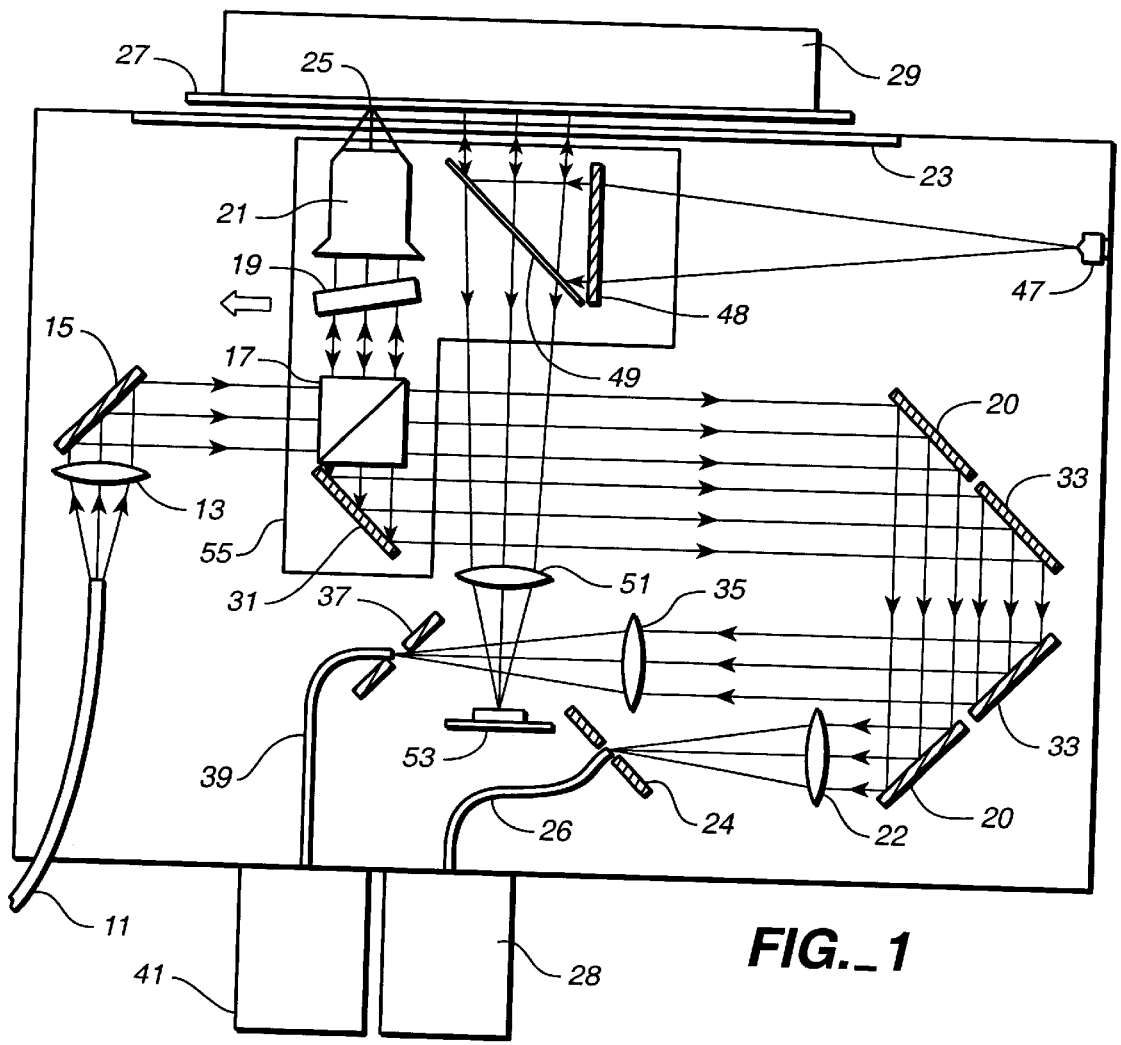
FIG._1

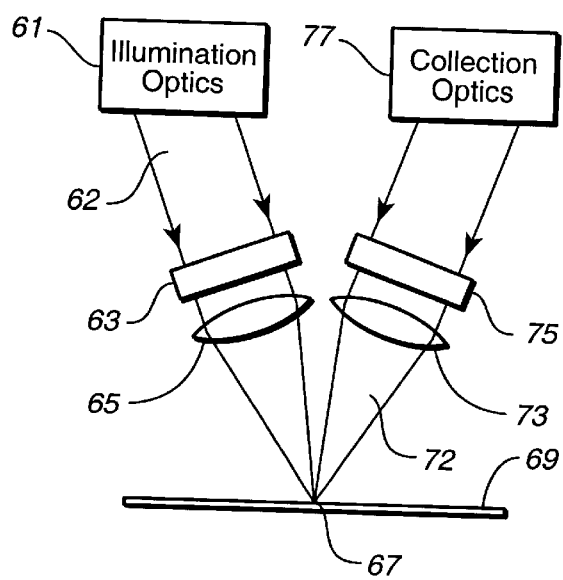
FIG._2
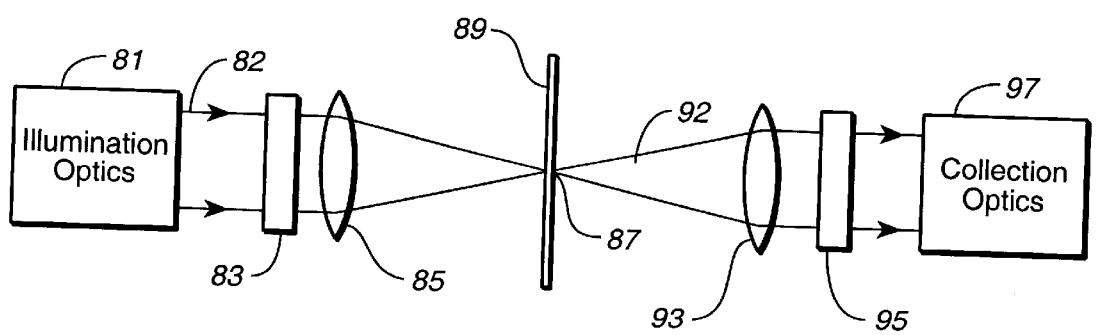
FIG._3

SMALL-SPOT SPECTROMETRY INSTRUMENT WITH REDUCED POLARIZATION

CROSS-REFERENCE TO RELATED APPLICATION

This application claims priority under 35 U.S.C. 119(e) from prior U.S. provisional application No. 60/226,396, filed Aug. 18, 2000.

TECHNICAL FIELD

The present invention relates to spectrometry instruments, spectroscopic reflectometers and transmissive spectrophotometers, and relates especially to those spectroscopy instruments which employ a microscope objective and associated imaging optical components for small-spot viewing of a sample having diffractive features to be measured.

BACKGROUND ART

Samples with grating-like structures will affect the amplitude and phase of the light they reflect or transmit differently for different incident polarizations. The same is also true for birefringent samples, or stacks of thin films at other than normal incidence. This can be an issue when making measurements with some photometric instruments. In lithography applications, for example, determining the linewidth or profile of diffractive pattern features formed on a semiconductor wafer or photomask may be performed by measuring the normal or near-normal incidence (hereafter collectively referred to as quasi-normal incidence) reflectivity or other optical properties with a small-spot reflectometer or small-spot transmissive spectrophotometer. The spectral reflectivity or transmissivity of the sample being measured will depend to some extent on the degree of polarization of the incident light and the orientation of the wafer.

In some instruments it is possible to orient the sample so that the grating-like structures of the pattern (or the optical axis of a birefringent surface or thin film stack) are presented in a known and consistent direction relative to the instrument's incident light. Any systematic errors due to polarization can then be minimized during data processing. That is, by carefully characterizing the polarization characteristics of the optics and modeling the effect on a sample's response at a particular sample orientation relative to the polarized light, the measured data can be processed so as to eliminate the polarization effect provided the sample is measured at the modeled orientation. However, it is not always possible to provide a specified sample orientation to the measuring instrument. Wafer handlers associated with lithography tracks frequently present the samples to the measuring instrument in a consistent but unknown orientation that the measuring instrument itself has no control over. Polishers produce a random sample orientation. Hence, it would be preferable if the instrument's illumination and collection optics were non-polarizing, so that orienting the wafer would be unnecessary.

In the past, the effect of instrument polarization on measurement results have been only a minor issue that has typically been ignored except in those instruments where polarization itself is the parameter being measured. Polarimeters and ellipsometers deliberately use incident light of known polarization. Also, until recently, spectrometry instruments were not used for measuring linewidth, profile, etc. of grating-like structures.

Unwanted polarization in the optics can be caused by polarizing elements such as tilted fold mirrors, beamsplitters, tilted glass surfaces, prisms, and spectrometer gratings. (In this context "polarizing" can mean partially polarizing or in some way affecting the polarization state.) One prior solution has been to reduce the polarization effect of instrument components by carefully arranging the planes of incidence of the tilted components in the system, so that for every such tilted component the instrument also has a similar component tilted in the perpendicular plane to cancel the polarization effect of the first. This use of component pairs requires more room for the optics, so that it cannot be used when a compact system is needed. The pairing technique cannot be used to alleviate the polarization effect in the spectrometer component of the system. In Zeiss monolithic spectrometers, among others, light is coupled with a fiberoptic bundle that scrambles the polarization.

Depolarizers of several types are known. Fiber depolarizers cannot be used in the imaging path because they would also scramble information about the image. Wedge depolarizers, comprising a birefringent wedge plate and an index-matched non-birefringent plate, need to be properly oriented to the polarization of the light to be depolarized. Because they produce a laterally offset double image, they are not well suited for imaging systems. Lyot depolarizers, comprising two non-wedge-shaped birefringent plates with their axes at 45_ to each other, are commercially available. They have previously been used in imaging spectroradiometers and spectropolarimeters for telescopes, for example on a satellite observing backscattered radiation from the earth to monitor atmospheric ozone depletion. In contrast to fiber and wedge depolarizers, Lyot depolarizers are image-preserving, and are therefore suitable for imaging systems.

An object of the present invention is to provide a small-spot spectrometry instrument with pattern viewing capability for measuring grating-like or other diffractive pattern structures on semiconductor wafers, photomasks, and the like, wherein the instrument's polarization effects on linewidth, profile, erosion and similar feature measurements are minimized.

SUMMARY OF THE INVENTION

The object has been met by a small-spot imaging, spectrometry instrument in which a polarization-scrambling element such as a Lyot depolarizer is incorporated between the beamsplitter and the microscope objective. The beamsplitter is the last significant polarizing element in the illumination path prior to the sample. Preferably the Lyot depolarizer is placed in a collimated portion of the light path to avoid creating a double image offset in focus. The Lyot depolarizer does not vary the polarization spatially as wedge depolarizers do. Rather, the Lyot depolarizer varies the polarization with wavelength. The sinusoidally perturbed spectrum that results can be removed by data processing techniques. If the depolarizer is made thick enough or made from a highlybirefringent material, such as calcite or alpha barium borate, than the sinusoidal perturbation may be much narrower than the wavelength resolution of the instrument. In this case the perturbation would not be detectable and no processing would be required to remove it. The only disadvantage of using calcite for the depolarizer material is that it does not transmit as much UV light as quartz. A disadvantage of alpha barium borate is its high cost. When both the illuminating and collected light pass through the same depolarizer, there is a preferred orientation for the depolarizer.

BRIEF DESCRIPTION OF THE DRAWINGS

FIG. 1 is a schematic plan view of a preferred embodiment of a spectrometry instrument according to the present invention.

FIGS. 2 and 3 are schematic plan views of two alternate embodiments of a spectrometry instrument according to the present invention, one a spectroscopic reflectometer with non-normal incidence and reflection and the other a transmissive spectrophotometer.

BEST MODE FOR CARRYING OUT THE INVENTION

With reference to FIG. 1, a preferred spectrometry instrument has a visible and UV light source (not shown) coupled to a source fiber 11. The light emerging from the instrument end of the fiber 11 is condensed by a lens 13 and directed by a fold mirror 15 to a beamsplitter 17. The lens 13 forms an image of the fiber end just after the fold mirror 15 to provide Kohler illumination for the objective 21. Rays that are collimated between the lens 13 and the objective 21 are focused to a point at the sample. A portion of the illumination light is transmitted through the beamsplitter to form a reference beam that is folded by mirrors 20, then focused by lens 22 to a pinhole aperture 24. Light passing through the pinhole is fed by a fiber 26 to a spectrometer component 28. The beamsplitter 17 reflects the other portion of the illumination light, which is directed through a Lyot depolarizer 19, then focused by a microscope objective 21 through a window 23 in the instrument to a small spot 25 on a sample 27. The beamsplitter is preferably a plate beamsplitter rather than a cube beamsplitter to avoid ghost reflections and degradation of the cement in UV light. The depolarizer 19 may be oriented at a slight angle to avoid reflection. The light between the beamsplitter 17 and depolarizer 19 should preferably be collimated to minimize aberrations. The support 29 for the sample 27 need not have any capability for orienting the sample.

Alternatively, the spectrometer could be replaced with a photodetector and the light source could be a scanning monochrometer. In this case, each wavelength band is measured sequentially.

The reflected light from the sample 27 is imaged by the microscope objective 21 to a spectrometer component 41 via the depolarizer 19, beamsplitter 17, folding mirrors 31 and 33, lens 35, pinhole mirror 37, and optical fiber 39. Adjoined to this instrument is a camera made up of an LED 47, a fresnel lens 48, a beamsplitting mirror 49, an imaging lens 51 and a CCD array 53. The camera may be used to locate a general area of interest on the sample for subsequent measurement by the microscopic spectrometer system. The microscope objective 21, Lyot depolarizer 19, beamsplitter 17 and a fold mirror 31, together with some of the camera optics, may be mounted together in a movable head 55 capable of translating in the X lateral direction. Movement in the other, Y, direction is accomplished by translation of the entire optical backplane shown in the diagram. Alternatively, the sample may be rotated (θ direction) and the optics moved along the radius of the sample. The remaining axis of lateral translation in the optics may be used to align the radial axis to the sample center of rotation. Focusing motion in a longitudinal (z) direction may be performed either by moving the objective 21 or sample support 29 or both.

Lyot depolarizers are commercially available, for example from Karl Lambrecht and other optical component manufacturers. They generally consist of two stacked plates of birefringent crystal material, such as quartz or calcite. The plates are both of uniform thickness, with one plate being twice as thick as the other. The thinner plate is usually 2 millimeters thick. The birefringent axes of the crystalline plate material are oriented so that one plate's axis is 45_ to the other plate's axis. The plates have a retardance that is strongly dependent on wavelength, so this type of depolarizer periodically varies the polarization versus the light's optical frequency. The polarization introduced by the rest of the optics in the system then produces a sinusoidal ripple on the measured spectrum. The period of this sinusoidal perturbation is nearly constant in terms of wavenumber, so if the data is averaged over intervals equal to integer multiples of the ripple period, the effect of the sinusoidal variation and thus of the instrument polarization is eliminated. Another way that the sinusoidal ripple effect can be mathematically eliminated during data processing is to regress to find the best-fit theoretical spectrum to the sinusoidally perturbed data assuming an ideal depolarizer. The best theoretical spectrum will naturally follow the middle of the perturbed spectrum. The perturbations may not be evident if the depolarizer is thick enough or made with calcite or alpha barium borate.

There are other possible designs for a polarization-scrambling element. For example, more than two plates can be used and different combinations of axes orientation or thickness can be used with nearly the same performance. A single plate can even be used if its optical axis is kept at 45 degrees to the polarizing direction of the sample. Any of these alternative designs can be use in place of, or in combination with, a Lyot depolarizer.

The polarization can also be effectively scrambled by varying the polarization state with time and averaging a detector signal over time. For example, the polarization state can be varied by rotating an optical element between the sample and other polarizing optics, as the signal is detected.

When the illumination and reflected light pass through the same depolarizer as is shown in FIG. 1, some sensitivity to the sample's rotational orientation occurs that varies only slowly with wavelength. This effect can be minimized by orienting the depolarizer so the thin plate is facing the wafer and the optical axis of the thicker plate is parallel to the plane of incidence on beamsplitter 17. This effect can also be minimized by covering part of the aperture of objective 21 with a depolarizer of a different thickness or orientation, but this will degrade the image quality slightly.

In addition to the use of the Lyot depolarizer, other techniques to minimize polarization, particularly in the imaging path, can include component pairing with perpendicular tilt planes and the use of spectrometers with polarization scrambling optical fibers. The Lyot depolarizer's main role is in ensuring depolarized illumination of the sample, and to depolarize the diffracted light from the sample before it interacts with any polarization sensitive components in the imaging path of the system.

With reference to FIGS. 2 and 3, the spectrometry instrument need not be a normal-incidence reflectometer as in FIG. 1, but could be modified for near normal spectroscopic reflectometry or for transmission spectroscopy. In each case, polarization can be varied with optical frequency by inserting Lyot depolarizers in the light paths. In FIG. 2, a non-normal incidence spectroscopic reflectometer differs from the spectroscopic reflectometer of FIG. 1 by having separate illumination and reflected light paths with a pair of microscopic objectives 65 and 73 and at least one and possibly two depolarizing elements 63 and/or 75. Illumination optics 61, corresponding for example to the optical fiber 11, condensing lens 13 and fold mirror 15 in FIG. 1, provide light 62 that is directed through a first Lyot depolarizer 63 and this focused by a microscope objective 61 to a small spot 67 on a sample 69. Light 72 reflected from the sample 69 is gathered by a second microscope objective 73, passed through a second Lyot depolarizer 75 to collection optics 77, corresponding for example to the elements 33–41 in FIG. 1 and including a spectrometer component like element 41 of FIG. 1. In FIG. 3, a transmissive spectrometry instrument for transmission samples 89 also has pairs of depolarizers 83 and 95 and microscope objectives 85 and 93 in separate illumination and collection light paths, which are located on opposite sides of the sample location. Illumination optics 81 provide light 82 whose polarization is varied with wavelength by the Lyot depolarizer 83, which is then focused by a microscope objective 85 to a spot 89 on the sample 89. Light 92 transmitted through the sample 89 is collected by objective 93, again depolarized 95 and sent to collection optics 97 that includes a spectrometer. One or more of the microscope objectives in any of the embodiments could be catadioptric, that is include mirror elements, in which case there may be some advantage to placing the depolarizers between the objective and sample location even though that positioning may increase chromatic aberration. Also, if either the illumination optics 61 or 81 or the collection optics 77 or 97 are such that they do not significantly polarize the light, then the depolarizer 63, 75, 83 or 95 could be removed from that path.

What is claimed is:

1. A spectrometry instrument for measuring properties of a sample, comprising:
    a sample support,
    a light source,
    a microscope system having illumination and collection light paths with at least one microscope objective in said illumination and collection light paths, components of said microscope system introducing polarization into said light paths, said microscope system characterized by having at least one, polarization-scrambling element located in at least one of said light paths between said polarization introducing components and said microscope objective, and
    a detector receiving a portion of light collected by said microscope system.

2. The instrument of claim 1 wherein the polarization-scrambling element is image-preserving.

3. The instrument of claim 2 wherein said detector is a spectrometer.

4. The instrument of claim 2 wherein said light source is a monochrometer.

5. The instrument of claim 3 wherein said polarization scrambling element comprises a Lyot depolarizer.

6. The instrument of claim 5 further comprising a data processor for receiving measurement data from said spectrometer, said processor eliminating wavelength dependent perturbations in the measurement data that are due to said Lyot depolarizer.

7. The instrument of claim 3 wherein at least some components of said microscope system are contained within a movable head.

8. The instrument of claim 3 wherein said microscope system is a reflectometer, said collection light path being a reflected light path for light directed onto a sample and reflected therefrom.

9. The instrument of claim 8 wherein said reflectometer is arranged for normal incidence and reflection of light with a single microscope objective in both of said illumination and collection light paths, said components introducing said polarization including a beamsplitter separating said illumination and collection light paths.

10. The instrument of claim 8 wherein said reflectometer is arranged for non-normal incidence and reflection of light.

11. The instrument of claim 3 wherein said microscope system is a spectrophotometer with components of said microscope system for said illumination and collection light paths being located on opposite sides of a sample location.

12. The instrument of claim 3 wherein said components introducing said polarization include a beamsplitter separating said illumination and collection light paths.

13. The instrument of claim 2 wherein the sample affects the polarization state of collected light.

14. The instrument of claim 13 wherein the sample is birefringent.

15. The instrument of claim 13 wherein the sample comprises a grating-like structure.

16. The instrument of claim 2 wherein the sample comprises a semiconductor wafer or photomask.

17. A reflectometry instrument for measuring properties of a sample, comprising:
    a microscope system having a microscope objective and with illumination and collection light paths passing through said microscope objective, components of said microscope system introducing polarization into said light paths, said microscope system characterized by having a polarization-scrambling element located in said light paths between the microscope objective and the polarization introducing components, and
    a spectrometer receiving a portion of light collected by said microscope system.

18. The instrument of claim 17 wherein the polarization-scrambling element is image-preserving.

19. The instrument of claim 18 wherein said polarization scrambling element comprises a Lyot depolarizer.

20. The instrument of claim 19 further comprising a data processor for receiving measurement data from said spectrometer, said processor eliminating wavelength dependent perturbations in the measurement data that are due to said Lyot depolarizer.

21. The instrument of claim 18 wherein at least some components of said microscope system are contained within a movable head.

22. A spectrometry instrument for measuring properties of a sample, comprising:
    a sample support;
    a light source;
    a microscope system having illumination and collection light paths with at least one microscope objective in said illumination and collection light paths, components of said microscope system introducing polarization into said light paths, said microscope system characterized by having at least one, image preserving Lyot depolarizer located in at least one of said light paths between said polarization introducing components and said sample support;
    a spectrometer receiving a portion of light collected by said microscope system; and
    a data processor for receiving measurement data from said spectrometer, said processor eliminating wavelength dependent perturbations in the measurement data that are due to said Lyot depolarizer.

23. A spectrometry instrument for measuring properties of a sample, comprising:
    a sample support,
    a light source,
    a microscope system having illumination and collection light paths, said collection light path being a reflected light path for light directed onto a sample and reflected therefrom and arranged for non-normal incidence and reflection of light with at least one microscope objective in said illumination and collection light paths, components of said microscope system introducing polarization into said light paths, said microscope system characterized by having at least one, image preserving polarization-scrambling element located in at least one of said light paths between said polarization introducing components and said sample support, and a spectrometer receiving a portion of light collected by said microscope system.

24. A spectrometry instrument for measuring properties of a sample, comprising:

a sample support, a light source, a microscope system having illumination and collection light paths with at least one microscope objective in said illumination and collection light paths, with components of said microscope system for said illumination and collection light paths being located on opposite sides of a sample location, and with components of said microscope system introducing polarization into said light paths, said microscope system characterized by having at least one, image preserving polarization-scrambling element located in at least one of said light paths between said polarization introducing components and said sample support, and a spectrometer receiving a portion of light collected by said microscope system.

25. A reflectometry instrument for measuring properties of a sample, comprising:

a microscope system having a microscope objective and with illumination and collection light paths passing through said microscope objective, components of said microscope system introducing polarization into said light paths, said microscope system characterized by having an image preserving Lyot depolarizer element located in said light paths;

a spectrometer receiving a portion of light collected by said microscope system; and a data processor for receiving measurement data from said spectrometer, said processor eliminating wavelength dependent perturbations in the measurement data that are due to said Lyot depolarizer.

* * * * *